(12) United States Patent
Rosenberg

(10) Patent No.: US 7,223,249 B2
(45) Date of Patent: May 29, 2007

(54) METHOD AND APPARATUS FOR DETERMINING THE DEPTH OF A GINGIVAL POCKET

(76) Inventor: Jeffrey M. Rosenberg, 428 Ballytore Cir., Wynnewood, PA (US) 19096

( * ) Notice: Subject to any disclaimer, the term of this patent is extended or adjusted under 35 U.S.C. 154(b) by 30 days.

(21) Appl. No.: 11/082,578

(22) Filed: Mar. 17, 2005

(65) Prior Publication Data
US 2006/0211954 A1    Sep. 21, 2006

(51) Int. Cl.
*A61B 5/103* (2006.01)
(52) U.S. Cl. ........................ 600/589; 600/587
(58) Field of Classification Search ............ 600/589, 600/590, 587; 433/72, 49, 56, 75, 119
See application file for complete search history.

(56) References Cited

U.S. PATENT DOCUMENTS

| | | | |
|---|---|---|---|
| 4,913,157 A | 4/1990 | Pratt, Jr. et al. | 128/661.03 |
| 4,941,474 A | 7/1990 | Pratt, Jr. | 128/660.01 |
| 4,951,677 A * | 8/1990 | Crowley et al. | 600/463 |
| 4,960,132 A | 10/1990 | Habekost | 128/776 |
| 5,100,318 A * | 3/1992 | Demyun et al. | 433/72 |
| 5,570,182 A | 10/1996 | Nathel et al. | 356/345 |
| 5,755,571 A | 5/1998 | Companion | 433/72 |
| 5,951,479 A * | 9/1999 | Holm et al. | 600/447 |
| 5,993,209 A * | 11/1999 | Matoba et al. | 433/72 |
| 6,050,821 A | 4/2000 | Klaassen et al. | 433/214 |
| 6,402,707 B1 * | 6/2002 | Ernst | 600/590 |
| 6,413,220 B1 | 7/2002 | Rose | 600/449 |
| 6,561,802 B2 | 5/2003 | Alexander | 433/29 |
| 6,638,219 B1 | 10/2003 | Asch et al. | 600/437 |
| 2004/0143186 A1* | 7/2004 | Anisimov et al. | 600/437 |
| 2006/0030778 A1* | 2/2006 | Mendlein et al. | 600/437 |

* cited by examiner

*Primary Examiner*—Max F. Hindenburg
*Assistant Examiner*—H. Q. Nguyen
(74) *Attorney, Agent, or Firm*—Duane Morris LLP

(57) ABSTRACT

A method and apparatus are provided for determining the depth of a gingival pocket using ultra-sound signals transmitted transgingivally. Transgingival (through the gum) transmission of the ultra-sonic signal permits a completely non-invasion determination of the dental health of an individual. In addition to determining the depth of a gingival pocket the health or disease of the pocket could be determined. The current invention allows for mapping of the underlying dental features of an individual for later comparison to future ultra-sound scans and to assist in fabrication of dental restorations.

14 Claims, 3 Drawing Sheets

METHOD AND APPARATUS FOR DETERMINING THE DEPTH OF A GINGIVAL POCKET

FIELD OF THE INVENTION

The present invention relates to the field of dentistry. More specifically, the present invention relates to a method and apparatus for assessing the periodontal health of an individual using ultra-sound imaging.

BACKGROUND

Periodontal disease (PD), which affects more than 60 million people, is the second most prevalent disease in the United States, yet less than one-fifth of Americans with periodontal disease receive treatment. Periodontal services require 150 million hours and $7 billion dollars annually. PD affects 80% of all adults and 90% of those between the ages of 55 and 64. It is estimated that 70 million adults suffer from some form of PD. Periodontal infections are now linked to cardiovascular disease, stroke, and diabetes making PD a serious health threat.

PD begins with a build up of plaque (which has bacteria in it) on a tooth. The bacteria in plaque attack the bone around the tooth, as well as the fibers (the periodontal ligament) that connect the tooth to the bone. As the fibers and bone are destroyed, a gingival pocket or space forms between the gum and the tooth—an ideal site for more plaque to build up. Left untreated, PD results in the destruction and recession of the periodontal ligament, which attaches the root of the tooth to the bone surface that makes up the interior of the tooth socket. The tooth attachments are destroyed in unpredictable site-specific pattern. Because public awareness of the disease is low and the early stages are painless, people generally don't floss that much, and as a result the disease progresses.

Unfortunately, because of the low awareness of the disease, it is generally not recognized until it has progressed to a significant degree. The treatment at this point, although effective, is uncomfortable, expensive, and often uncovered by insurance.

The accepted standard for measuring the progression of PD is to probe the gingival pocket to measure its depth and thereby measure the degree of recession of the periodontal ligament. The current gold standard for this measurement is a small ruler called a periodontal probe that is "poked" into the gum line to find and measure periodontal pockets and gum line detachments. The process is slow and painful, taking 10-15 minutes for some 180 measurements. Further, unless an automated recording system is used, the process requires the participation of two persons, one to take the measurements and a second to record the measurements. Recording of measurements is necessary to compare readings from one date to another to see if a pocket is breaking down. Because this is a tedious and painful process that is seldom done accurately or to completion, it is difficult to accurately identify and track the progress of the disease. The result is that the disease progresses insidiously and continually.

In addition to manual probing, another approach is disclosed in U.S. Pat. No. 5,755,571 to Companion. The probe disclosed in this patent uses intra-sulcular ultra-sound waves projected along the surface of the tooth for determining periodontal pocket depth. This method is less invasive with the mechanism, but injects a stream of water into the pocket to act as a transmission medium for ultra-sound waves. In addition to being a generally messy process, the injection of water into the root area of a tooth infected with PD can be the source of additional irritation of the area and discomfort to the patient. In addition, the water stream theoretically could mobilize the bacterium and cause cross contamination of sites. Further, the probe disclosed in Companion requires a fixed reference point, and uses the cemento-enamel junction (CEJ) as that reference point. The CEJ is the junction point between the enamel crown of a tooth and the cementum that makes up the root of the tooth. Establishing this reference point requires the use of an invasive probe that is incorporated with the ultra-sonic probe. Further, as disclosed in Companion, the CEJ is often difficult to locate or not present at all due to human variation and/or destruction of the CEJ.

A device known as the Florida probe uses a spring-loaded mechanism to detect the CEJ. Manual probing and the Florida probe are similar in that they invade the pocket to the base and make measurements from contact with the tissue at the bottom of the pocket. While considered to be superior to standard manual probing techniques, the Florida probe suffers from the same drawback as standard probing in that it is extremely invasive. In fact, the spring loaded mechanism of the Florida probe results in greater pressure being applied, and hence greater irritation to the gingival pocket. Further, the Florida probe suffers the same limitation as manual probing in that the presence of tartar in the pocket area may result in the determination of a false bottom for the pocket.

All of these methods approach the measurement of gingival pocket depth by varying levels of invasive measurement and are therefore likely to be uncomfortable for the patient and could prove cause for cross contamination.

U.S. Pat. No. 6,413,220 to Rose discloses a method and apparatus for using ultra-sonic waves for measuring the depth of a detachment between a tooth and its supporting tissue. Like the probe disclosed in Companion, the apparatus disclosed by Rose projects an intra-sulcular ultra-sound wave along the surface of a tooth (surface acoustic wave pulse) to determine pocket depth. The method and apparatus of Rose depend on achieving a particular critical angle of incidence between the tooth surface and the ultra-sonic probe. Therefore, repeatability of this method is highly dependent upon the skill of the operator.

Therefore, a need exists for a non-invasive method and apparatus for the identification and tracking of periodontal disease. Such a method would measure periodontal pocket depth non-invasively, and thereby enhance patient comfort. Therefore the method would reduce patient fears regarding examination of the gums and thereby make the public more likely to seek out the appropriate care and obtain early diagnosis and treatment. Such a method would further be easy to use, equivalent in complexity and time of use to current manual probes. Such a method would thereby offer repeatability, and the ability to track patient gum health, and given the new evidence of the relation of PD to systemic disease, make a serious improvement to public health.

SUMMARY OF THE INVENTION

The current invention uses a precise ultra-sonic probe to painlessly, non-invasively, and accurately measure the periodontal pockets. Many pockets can be done at once and automatically recorded to allow comparative analyses of data thereby detecting periodontal disease (PD) much earlier. The current invention thereby revolutionizes PD treatment by telling the dentist, doctor, and patient when and where to treat PD very early and very accurately. Further, because of public familiarity with other uses of ultra-sound, the current invention may lead to increased demand for services and thereby lead to a better understanding of PD on the part of the public.

The current invention achieves this by providing a method for determining the depth of a gingival pocket. The method comprises transmitting a transgingival ultra-sonic signal through the gum of an individual at the location of a gingival pocket and receiving at least one reflected ultra-sonic signal in a raw waveform. The raw waveform is processed into a processed waveform. The time of flight between transmission of the ultra-sonic signal and reception of the at least one reflected ultra-sonic signal is measured, wherein the depth of a gingival pocket is determined by the time elapsed between the transmission of the ultra-sonic signal and the reception of the at least one reflected ultra-sonic signal. The amplitude of the at least one reflected ultra-sonic signal is measured, wherein the density of a material from which a reflected ultra-sonic signal is received is determined by the amplitude of the reflected signal.

In another embodiment, the current invention provides an apparatus for measuring the depth of a gingival pocket. The apparatus comprises a probe comprising at least one transducer having a pulsed transmitter for transmitting an ultra-sonic signal. The at least one transducer is mounted in the tip of a control arm. The apparatus further comprises at least one gated or un-gated receiver for receiving at least one reflected ultra-sonic signal. The apparatus also has a data processing unit for converting the at least one reflected ultra-sonic signal from a raw waveform to a processed waveform. According to a preferred embodiment, a registration guide sized and configured to fit over the gums of an individual is provided. The registration guide has a plurality of channels therein, the channels being spaced apart to correspond to the locations of gingival pockets in the gums of an individual. Each of the channels is sized and configured to receive the tip of the control arm.

DETAILED DESCRIPTION OF THE INVENTION

Figure 1:
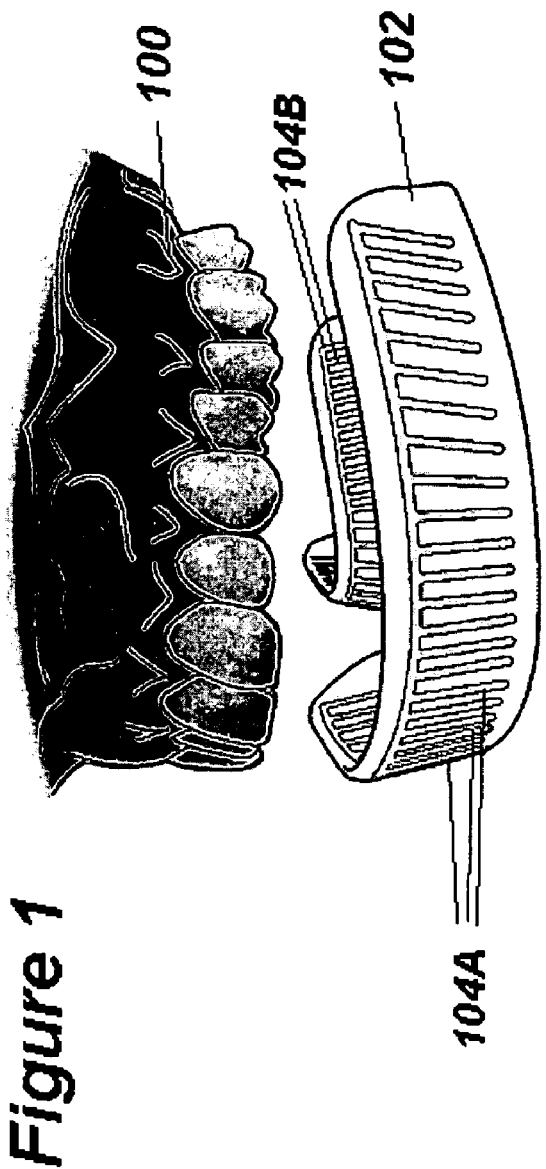
FIG. 1 Illustrates a registration guide according to the invention for the upper gums of an individual.

In its broadest sense the current method comprises transmitting an ultra-sonic signal through the gum tissue of an individual (transgingivally), as opposed to intra-sulcularly, using an ultra-sonic probe and receiving signals reflected from the gum tissue and underlying structures, wherein the time of flight of the reflected signals and their relative amplitude can be used to determine the topography of the underlying dental structures.

According to another embodiment of the invention an apparatus for executing the method is provided. In its broadest sense the apparatus comprises an ultra-sonic probe comprising a transducer for emitting an ultra-sonic signal and acquiring a reflected signal. The apparatus further comprises a pulsed transmitter for generating ultra-sonic signals, at least one gated or un-gated receiver for receiving reflected signals in raw waveform, and a processor for processing the raw waveform to a processed waveform which can be used to determine the topography of the underlying dental structures.

In general, the use of ultra-sound signals to elucidate the internal structures of human and other live subjects takes advantage of the fact that the degree to which a sound wave is absorbed, propagated or reflected by any structure is a function of the density of that structure. For instance, the soft tissue of a human or other live subject has a greater tendency to absorb, rather than propagate or reflect a sound wave, as opposed to a hard bony or tooth structure. Similarly, on the same scale, soft tissue will provide at least some degree of propagation or reflectance, whereas an empty space, such as a gingival pocket will provide a negligible or no reflected or propagated wave. Reflected waves can also be generated by a transition in the density of a structure, such as the boundary between soft gum tissue and hard tooth or bone. Also important to the use of ultra-sonic signals is the fact that as a signal encounters either soft or hard tissue, it is attenuated by absorption of some of the energy of the signal.

The application of such ultra-sound techniques to the determination of dental structures has been disclosed by previous authors. For example, U.S. Pat. No. 5,755,571 to Companion discloses a probe, which uses ultra-sound waves projected into the crevice between the tooth and gum tissue (the sulcus) along the surface of the tooth for determining periodontal pocket depth. The method of Companion injects a stream of water into the pocket to act as a transmission medium for ultra-sound waves. In Companion, an ultra-sonic wave projected along the surface of a tooth is reflected by the hard structure of the joining of the gum to the tooth. A draw back of this method is that a reference point needs to be established where the pocket depth is measured to gauge the change in depth of the pocket at a location over time.

The advantage of the current invention over previously disclosed methods is that it is a transgingival technique, which transmits energy across the gum tissue rather than behind it. This approach is virtually non-invasive to the patient and can be much more comfortable and less likely to transfer the bacteria of the pocket. The inventor has discovered that the topography of dental structures can be efficiently determined by projecting an ultra-sonic wave through the gum tissue of an individual rather than along the surface of the tooth. The current method eliminates the need to inject water into the gingival pocket to act as a transmission medium. Further, the method according to the current invention eliminates the need to establish a reference point for measurement by manual probing as the reference point is part of the transgingival signal. For example, the cemento-enamel junction can be detected based on the variation in the reflected ultra-sonic signal that occurs at the transition from the enamel of the tooth crown to the cementum of the tooth root. The current method still allows data to be compared to data of known periodontal pathological situations thereby learning more about the condition of the pocket.

The invention will now be described more fully with reference to exemplary drawings. According to the method of the current invention, an ultra-sonic signal is transmitted transgingivally. The ultra-sonic signal is transmitted using an ultra-sonic probe having a transducer which can function to acquire reflected ultra-sonic waves, as well as emit the transmitted signals. In a preferred embodiment the probe has two transducers; one to emit an ultra-sonic signal and the other to acquire reflected signals. Once transmitted from the probe, the ultra-sonic signal will be reflected and further propagated to varying degrees. A portion of the signal will be reflected from the gum surface and be acquired by the probe as a reflected ultra-sonic signal. Another portion of the signal will be further propagated through the gum tissue. In the case that a void, comprising the gingival pocket is located adjacent to the opposite side of the gum tissue into which the ultra-sonic signal is transmitted, no further reflected signal will be acquired past the boundary as the void space will not further propagate the ultra-sonic signal. However, in the event that the ultra-sonic signal propagated through the gum tissue encounters a transition to a structure of a greater density, a further reflected signal will be generated and therefore acquired by the probe. The intensity of the reflected signal acquired from the internal gum boundary will depend on whether the boundary layer is with the empty space of the gingival pocket or with the connection point of the gum to the tooth. According to the preferred embodiment of the current invention, the portion of the ultra-sonic signal propagated through the gum tissue encounters the attachment point of the root of a tooth to the soft tissue of the gum, which represents the bottom of a gingival pocket, and thereby generates a reflected signal. In terms of the visualization of the data acquired according to the method, the areas comprising the gingival pocket will appear as "dark" whereas the location of the tooth attachment, and hence the bottom of the pocket, will appear as relative "bright" spots.

According to the current invention, by probing the gum surface at varying depths from the gingival margin, the attachment point of a given tooth, and therefore the depth of the gingival pocket at that tooth, can be determined. Further, it is possible to determine further dimensions and topography of the pocket, for example whether the pocket is narrow or broad, or the degree to which the increased depth of a pocket has spread around the circumference of a tooth.

Figure 2:
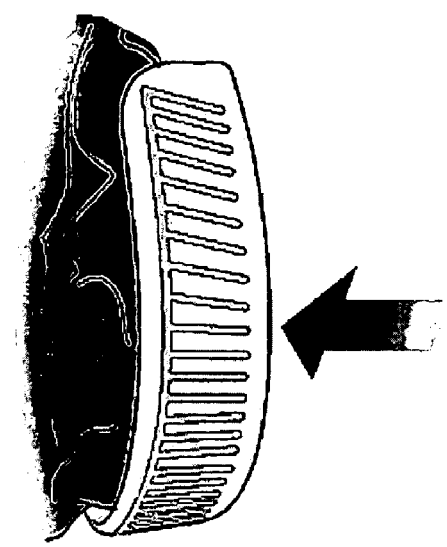
FIG. 2 Illustrates a registration guide according to the current invention installed over the upper gums of an individual FIG. 3 Illustrates an ultra-sonic probe according to the current invention being used in conjunction with a registration guide in the method according to the current invention.

According to a preferred embodiment of the method, a registration guide is used to aid in precisely locating the areas to be probed. Referring to FIGS. 1 and 2, a registration guide 102 is shown, which is sized and configured to fit over the gums of an individual 100. The exterior surface of the registration guide, which comprises the areas in front of, as well as in back of the teeth. The front of the registration guide has a plurality of guide channels 104A therein, and the back has a second plurality of guide channels 104B. Individual registration guides can be prepared to fit the upper and lower arch of an individual, and can also be sized to small, medium or large individuals. In a preferred embodiment of the current invention, the registration guide is a disposable one-use component.

Figure 3:
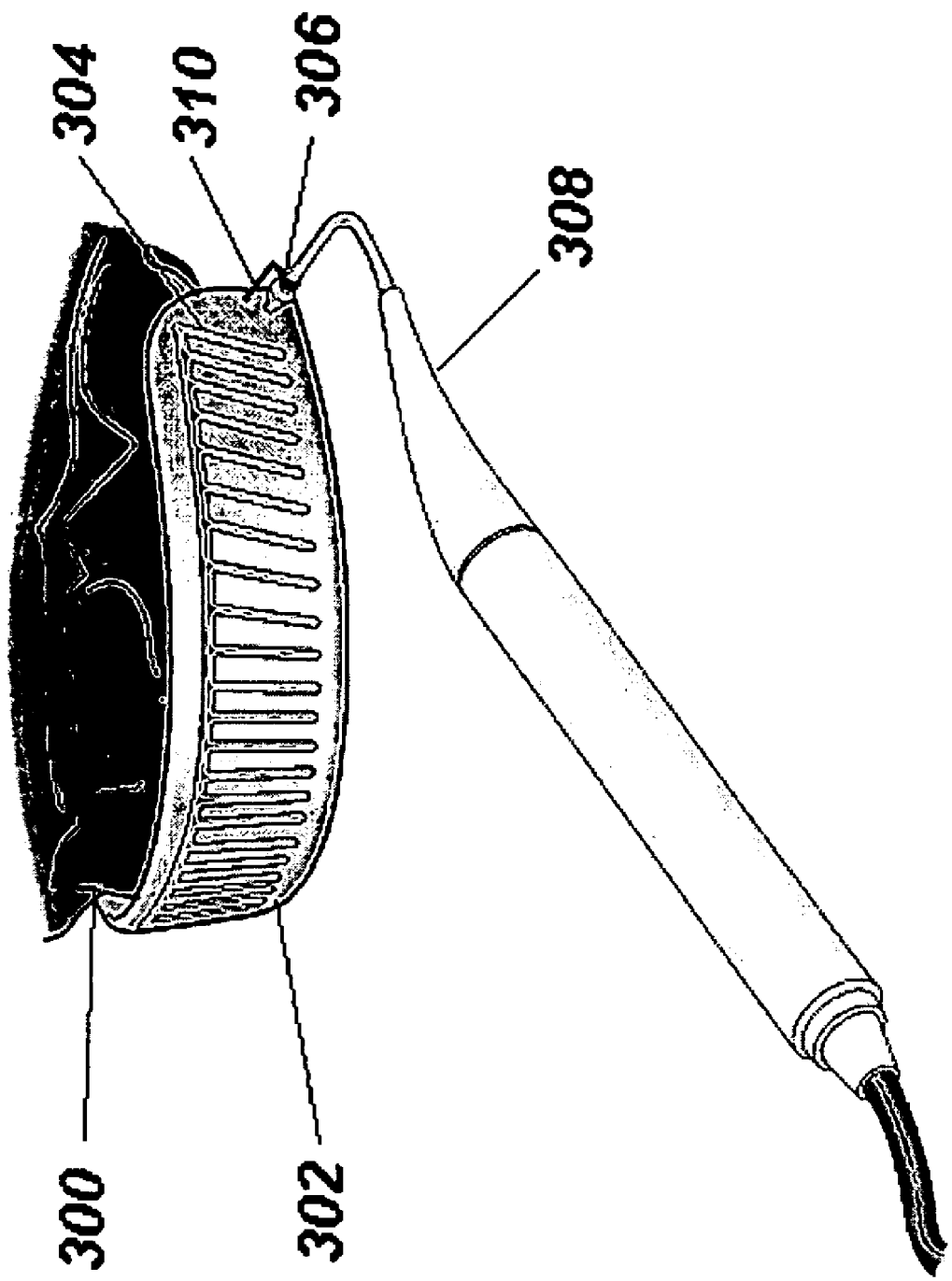

Referring to FIG. 3, a registration guide 302 is shown inserted over the gums of the upper jaw 300 of an individual. The guide channels 304 are sized and configured to receive the tip 306 of the ultra-sonic probe 308. The guide channels 304 ensure that the proper angle of incidence of the ultra-sonic signals is achieved, as well as ensuring precise and repeatable measurement of each gingival pocket. In a preferred embodiment, the ultra-sonic probe 306 has a guide arm 310, which further helps to ensure that the proper angle of incidence of the ultra-sonic signals is achieved, as well as ensuring precise and repeatable measurement of each gingival pocket.

Figure 4:
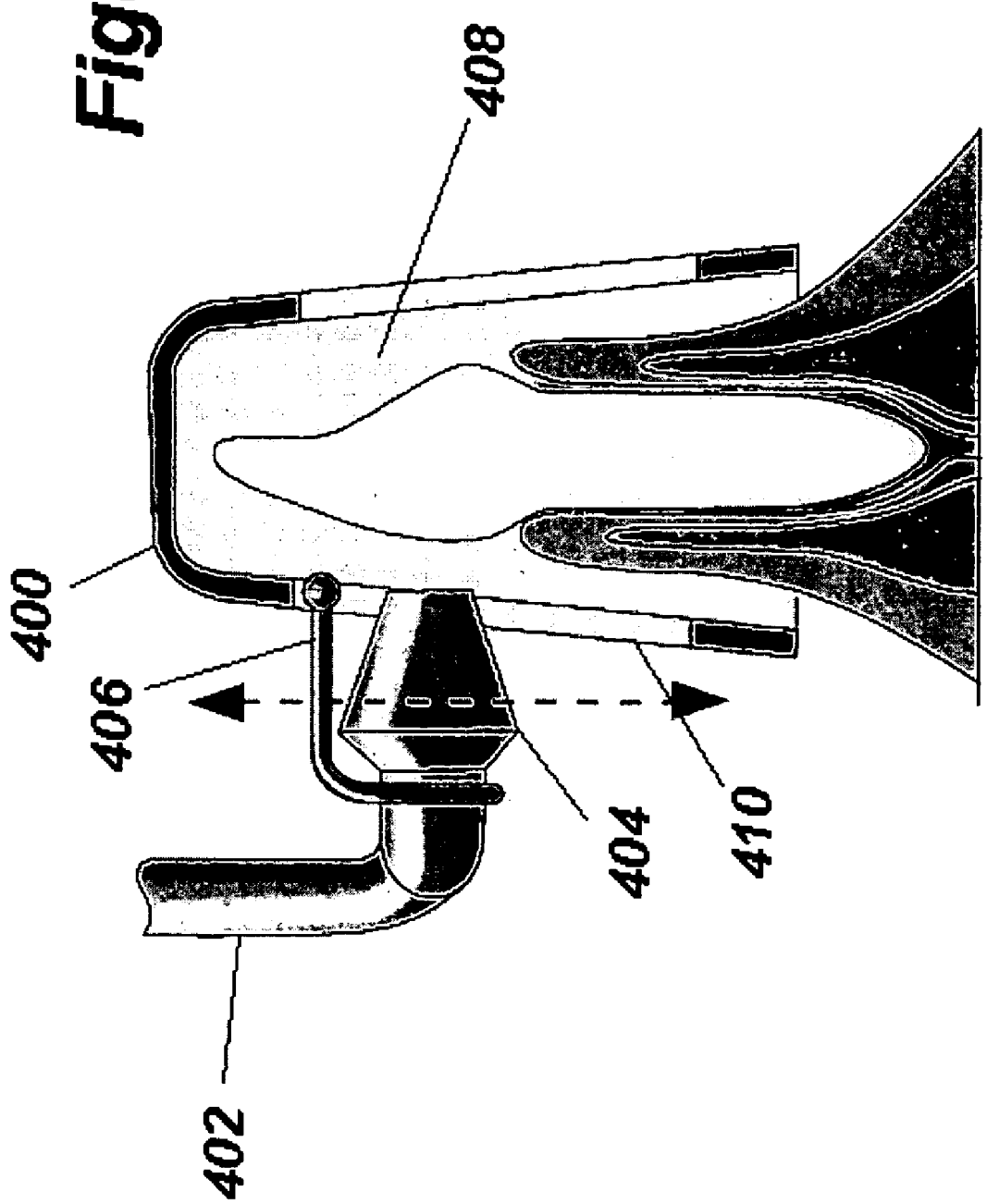
FIG. 4 Illustrates an alternate view of an ultra-sonic probe according to the current invention being used in conjunction with a registration guide in the method according to the current invention

Referring to FIG. 4, an alternate view of a registration guide 400 being used in conjunction with an ultra-sonic probe 402 according to the current invention is shown. The tip 404 of the ultra-sonic probe and the guide arm 406 fit into the guide channel 410 to ensure the proper location and orientation of the transducer. The probe tip 404 can be moved within the guide channel 410 as illustrated in FIG. 4 to permit probing at various depths along the gum line, thereby visualizing the underlying dental structures at various depths and identifying the CEJ reference point, which can be placed in a look-up file. If the CEJ has been obliterated by a restoration, that material will have a look-up reference as well. Still referring to FIG. 4, the space between the inner surface of the registration guide and the gums and teeth is filled with a soft media 408 that will conform to the shape of the gums and teeth, and be a good transmission medium for ultra-sonic signals. The media is preferably a gel or colloidal material.

The ultra-sonic probe itself comprises a transducer mounted in the tip of a control arm for ease of handling. Preferably, the control arm is flexible to permit easy adjustment of the angle of incidence of the ultra-sonic signal. A pulsed transmitter in electrical connection to the transducer generates an electrical signal, which is converted to an ultra-sonic signal by the transducer. Preferably, the probe operates in the range of 10 to 25 MHz. The transducer also acquires ultra-sonic signals that are reflected by underlying dental structures. One or more receivers, also in electrical connection with the transducer receive the reflected signals acquired by the transducer in raw waveform. The one or more receivers may be gated or un-gated. Preferably, the receivers are gated, which permits the scanning of discrete time intervals, which are established based on the expected time of flight of a signal between when it is generated and a reflected signal is received. For example, based on the estimated thickness of the gum tissue of an individual, which is relatively uniform throughout the population, an estimated time of flight for an ultra-sonic signal reflected from an underlying dental structure can be estimated. Using this estimated time of flight, a gated receiver can be programmed to receive data at only fixed intervals corresponding to the estimated time of flight. In this way a substantial amount of noise can be eliminated when scanning dental structures.

In a preferred embodiment, the probe has at least two transducers located in the tip of the control arm. A first transducer is in electrical connection to a pulsed transmitter for emitting an ultra-sonic signal. A second transducer is in electrical connection to a gated or ungated receiver for receiving a reflected ultra-sonic signal in raw waveform.

A processor then processes the raw waveform to produce a processed waveform that can be used to visualize underlying dental structures as well as evidence of pathology such as bleeding, inflammation, or exudate. The processor can be any computer processor capable of performing data transformation. Those skilled in the art will be familiar with methods for transforming raw ultra-sonic signals to a processed waveform. The particular transform method used is not critical to the invention, and therefore all methods are considered within the scope of the invention. The transformed data is then stored in a database for comparison to other measurements taken over time.

Preferably the ultra-sound technique used by the probe is A-Scan ultra-sound, which is a simple 1-axis technique. Other ultra-sound techniques, such as B-Scan and A/B-Scan are also considered within the scope of the invention.

It is contemplated that the method and apparatus of the current invention will have multiple applications in the area of dentistry beyond the determination of the depth of a gingival pocket. For example, it is contemplated that the method and apparatus of the current invention could be used to map the dental structures of an individual, such as the location of teeth, restorations, and other landmarks. The initial mapping could then be used as an impression on an ongoing basis to determine the progression of cracks, fractures, cavities and other conditions of both hard and soft tissue, and relate to the articulation of the upper and lower dental arches. This mapping could assist in fabrication of dental restorations. It is also contemplated that the signal data can be used for comparisons to know pathological pocket conditions such as inflammation or infection, thereby portraying not only the depth of the pocket, but the physiologic condition of the pocket as well. Thus, the invention in not limited to the specific embodiments presented here.

The invention has thus been described in detail with reference to exemplary drawings. Those skilled in the art will recognize that the invention is not limited to those examples provided herein. The full scope of the invention will be clear from the claims appended hereto.

What is claimed is:

1. A method for determining the depth of a gingival pocket, comprising:
    placing a registration guide over gums and teeth of an individual and locating at least one ultrasonic probe relative to the registration guide so as to direct the probe inwardly through a gum to at least part of the gingival pocket,
    transmitting a transgingival ultra-sonic signal through the gum of the individual toward the gingival pocket,
    receiving at least one reflected ultra-sonic signal in a raw waveform affected by the gingival pocket, and,
    processing the raw waveform to determine the depth of the gingival pocket along the registration guide.

2. The method according to claim 1, wherein the ultrasonic signal is transmitted and the reflected ultra-sonic signal is received by a probe comprising at least one transducer mounted in an arm, a pulsed transmitter, and at least one receiver.

3. A method for determining the depth of a gingival pocket, comprising:
    transmitting a transgingival ultra-sonic signal through the gum of an individual at the location of a gingival pocket,
    receiving at least one reflected ultra-sonic signal in a raw waveform,
    processing the raw waveform into a processed waveform,
    measuring the time of flight between transmission of the ultra-sonic signal and reception of the at least one reflected ultra-sonic signal,
    measuring the amplitude of the at least one reflected ultra-sonic signal, wherein the depth of a gingival pocket IS determined by the time of flight of the ultra-sonic signal, and the amplitude of the at least one reflected ultra-sonic signal, wherein the ultra-sonic signal is transmitted and the reflected ultra-sonic signal is received by a probe comprising at least one transducer mounted in a tip of a flexible arm, a pulsed transmitter, and at least one gated or un-gated receiver, and
    placing a registration guide over the gums and teeth of the individual, and placing the tip of the flexible arm against the registration guide such that the transmitted and reflected signals travel through a wall of registration guide.

4. The method according to claim 3, wherein the registration guide comprises an outer surface and an inner surface, the outer surface of the registration guide having a plurality of guide channels therein, the guide channels being sized and configured such that a tip of the flexible arm is received by a guide channel and can be moved within the guide channel, a void space between the inner surface of the registration guide and the gums and teeth of the individual is filled with a soft media capable of propagating an ultrasonic signal, the plurality of guide channels being spaced apart on the outer surface of the registration guide to correspond to locations of gingival pockets, and a topography of at least one of the gingival pockets is mapped by transmitting and receiving a plurality of ultra-sonic signals at various locations within selected said guide channels.

5. The method according to claim 4, wherein, the probe further comprises a registration arm affixed to the flexible arm proximal to the tip of the flexible arm, the registration arm being sized and configured to be received by a guide channel in the registration guide.

6. The method according to claim 1, wherein the ultrasonic signal comprises A-Scan ultra-sound.

7. The method according to claim 4, wherein the soft media comprises at least one of a gel and a colloidal material.

8. An apparatus for measuring the depth of a gingival pocket, comprising:
    a probe comprising a transducer mounted in a tip of a control arm,
    a pulsed transmitter for transmitting an ultra-sonic signal,
    at least one receiver for receiving at least one reflected ultra-sonic signal,
    a data processing unit for converting the at least one reflected ultra-sonic signal from a raw waveform to a processed waveform,
    a data storage unit for storing at least one of raw waveform data and processed waveform data, a registration guide sized and configured to fit over gums and teeth of an individual, the registration guide having an inner surface and an outer surface, the outer surface having a plurality of guide channels therein, the guide channels being spaced apart to correspond to locations of gingival pockets in the gums of the individual, each of the guide channels being sized and configured to receive part of the probe, and a soft media for filling a void space between the inner surface of the registration guide and the gums and teeth of the individual.

9. The apparatus according to claim 8, wherein the control arm is flexible.

10. The apparatus according to claim 8, wherein the probe further comprises a registration arm mounted proximal to the tip of the control arm, the registration arm being sized and configured to be received by a guide channel in the registration guide.

11. The apparatus according to claim 10, wherein the registration arm and the control arm are configured such that the tip of the control arm and the registration arm are both received by a same said guide channel in the registration guide.

12. The apparatus according to claim 8, comprising two transducers mounted in the tip of the control arm, wherein a first of the transducers is in electrical connection with the pulsed transmitter and a second of the transducers is in electrical connection with the at least one receiver.

13. The apparatus according to claim 8, wherein the transmitter and receiver comprise A-Scan apparatus.

14. The apparatus according to claim 8, wherein the soft media comprises at least one of a gel and a colloidal material.

* * * * *